United States Patent [19]

Kopatz et al.

[11] 3,970,022
[45] July 20, 1976

[54] METHOD AND APPARATUS FOR STITCHING STRING TO FOAM USED IN TAMPONS

[75] Inventors: William H. Kopatz, Levittown; Rey W. Cooper, Bryn Athyn; Russell W. Watson, Hatboro, all of Pa.

[73] Assignee: W. R. Grace & Co., New York, N.Y.

[22] Filed: May 7, 1975

[21] Appl. No.: 575,198

Related U.S. Application Data

[63] Continuation-in-part of Ser. No. 575,200, May 7, 1975.

[52] U.S. Cl. .............................. 112/265; 112/104; 112/121.19; 289/18
[51] Int. Cl.² .......................................... D05B 3/12
[58] Field of Search ............... 112/1, 2, 3 A, 429, 112/430, 435, 436, 58, 79 R, 104, 121.14, 121.15, 121.19, 130, 156, 163, 185, 187, 198, 223, 252, 254, 262, 265; 289/1.2, 1.5, 2, 18

[56] References Cited
UNITED STATES PATENTS

| | | | |
|---|---|---|---|
| 2,715,374 | 8/1955 | Carrier | 112/121.19 |
| 2,769,413 | 11/1956 | Bodard | 112/121.19 |
| 3,348,866 | 10/1967 | Etz | 289/18 |
| 3,814,469 | 6/1974 | Simon | 289/1.5 |

*Primary Examiner*—G. V. Larkin
*Attorney, Agent, or Firm*—Silverman and Jackson

[57] ABSTRACT

A method for attaching a length of string to a segment of material such as a foam pre-form used in tampon manufacture comprising providing the string in proximity to the pre-form, drawing the loose ends of the string through the pre-form in intersecting divergent perpendicular directions to form a loop on the side of their entry into said pre-form, whereby the loose ends protrude therefrom, passing the protruding ends through the loop, and tightening the loop around the ends to form a knot. The apparatus useful in the above method comprises a pair of reciprocable needles adapted to extend into perpendicular intersection with the pre-form to engage and retract a length of string through said pre-form, a string tensioning means for placing said string in tension adjacent said pre-form, means in alignment with said tensioning means for severing a finite length of said string, and means laterally aligned with said pre-form and axially aligned with said needles for drawing the ends of said string into a knot.

15 Claims, 14 Drawing Figures

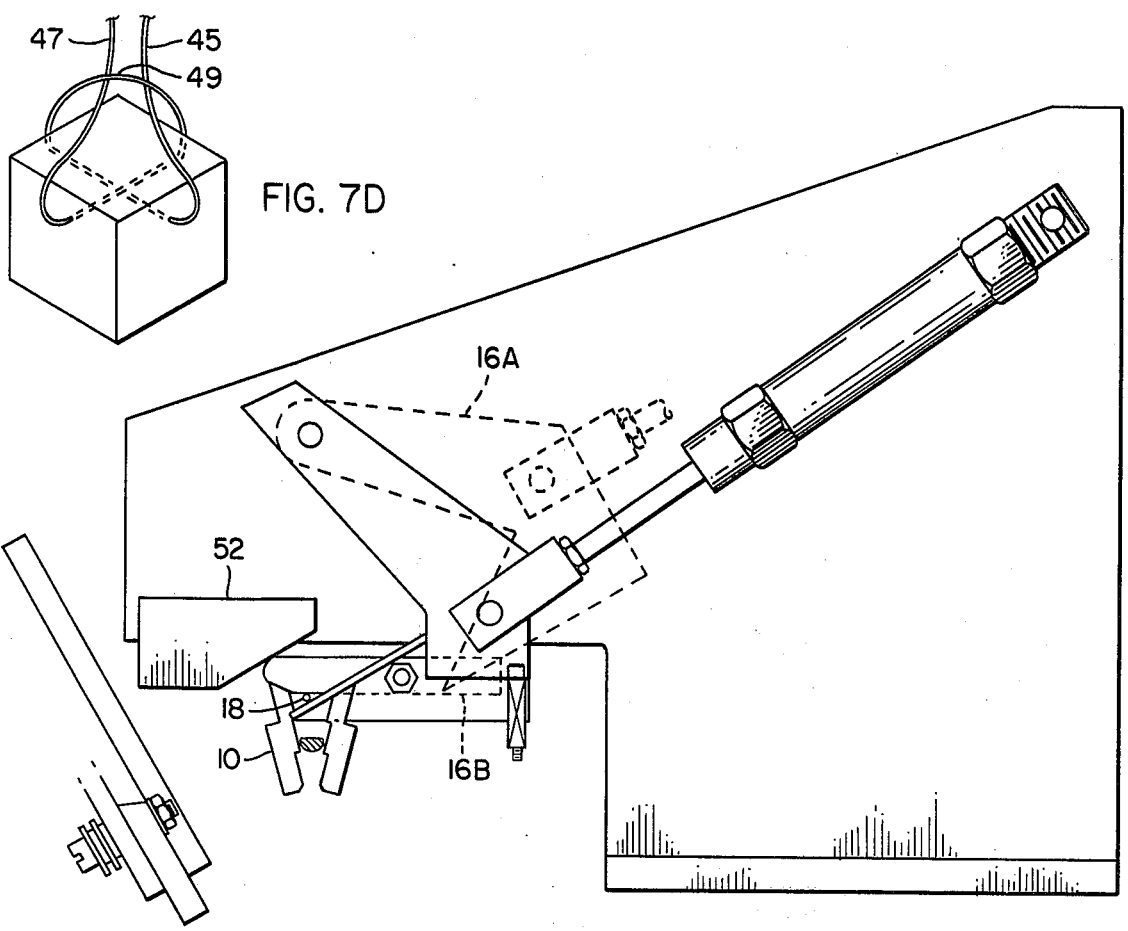
FIG. 7D
FIG. 10
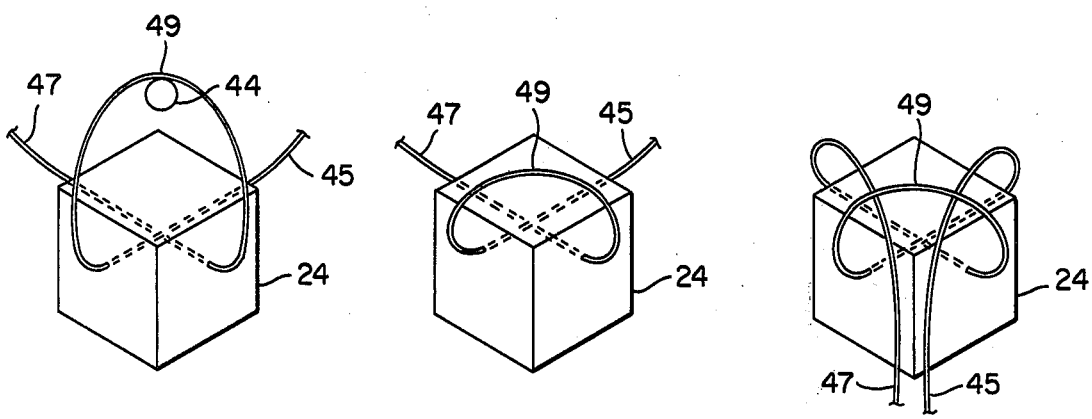
FIG. 7A
FIG. 7B
FIG. 7C

METHOD AND APPARATUS FOR STITCHING STRING TO FOAM USED IN TAMPONS

CROSS-REFERENCE TO RELATED APPLICATION

The present application is a continuation-in-part of co-pending application Ser. No. 575,200 filed of even date herewith by the inventors herein, for "METHOD AND APPARATUS FOR THE PREPARATION OF CATAMENIAL DEVICES."

BACKGROUND OF THE INVENTION

The present invention relates to a special purpose stitching apparatus. More particularly, the instant invention relates to an apparatus intended for use in the securement of string to a volume of hydrophilic foam intended for use in a catamenial device such as a woman's tampon.

One consideration which has led to the present area of inventive effort is that of the rate or speed at which the presently required types of special purpose stitching must be performed. That is, in terms of practical manufacturing needs, it is necessary to attain a production rate on the order of thousands of stitching operations per minute. Accordingly, many prior art approaches to the stitching problems herein involved may have been adequate for achieving a stitching of the present nature, however, at lower production rates than are required by present day production and management standards.

Also, the particular stitching, looping and tying functions required in the manufacture of the present hydrophilic foam tampon are sufficiently complex so as to preclude their repetition at desired rates, if prior art machinery were utilized.

It is to be noted that the present invention relates to a sub-system of a larger production apparatus utilized in the general preparation and fabrication of catamenial devices. Said apparatus is presently the subject of a parent application Ser. No. 575,200, filed on May 7, 1975, entitled METHOD AND APPARATUS FOR PREPARATION OF CATAMENIAL DEVICES, which application is herein incorporated by reference.

SUMMARY OF THE INVENTION

In accordance with the present invention, a method and apparatus are disclosed for the attachment of a finite length of string to a segment of material such as a foam pre-form used in tampon manufacture.

The method briefly comprises providing the string in proximity to the pre-form, drawing the loose ends of the string through the pre-form in intersecting divergent perpendicular directions to form a loop on the side of their entry into said pre-form whereby said loose ends protrude from said pre-form, passing said protruding loose ends through said loop, and tightening said loop around said ends to form a knot.

The apparatus for use in the method of the invention comprises a pair of reciprocable needles adapted to extend into perpendicular intersection with the pre-form to engage and retract a length of string through said pre-form, a string tensioning means for placing said string in tension at a location tangentially adjacent said pre-form and distal to said needles, means in alignment with said tensioning means for severing a finite length of said string, and means axially aligned with said needles and distally displaced therefrom beyond said tensioning means, for drawing the ends of said finite length of string into a knot.

The method and apparatus of the present invention facilitate the rapid attachment of withdrawal string to tampons, particularly those prepared from hydrophilic polyurethane foams such as those disclosed in co-pending applications Ser. Nos. 575,356 and 575,348 filed of even date herewith, the disclosures of which are incorporated herein by reference.

Accordingly, a principal object of the present invention is to provide a high-speed special purpose stitching, looping, and tying apparatus.

Another object is to provide a high-speed apparatus of the above type especially adapted for usage with hydrophilic foams.

A yet further object is to provide a high-speed stitching device capable of achieving a desired looping and tightening of the stitched string within the hydrophilic foam of a tampon.

The above and further objects of the present invention will become evident from a consideration of the description which follows with reference to the accompanying figures.

BRIEF DESCRIPTION OF THE DRAWINGS

FIGS. 7A, 7B, 7C and 7D are schematic illustrations of four successive steps in the stitching, looping and tightening operation performed upon the stitched foam.

FIG. 10 is a schematic view of one embodiment of the string cutting mechanism of the present invention, also symbolically illustrated in FIG. 3 as scissor 16.

DETAILED DESCRIPTION OF THE INVENTION

Figure 1:
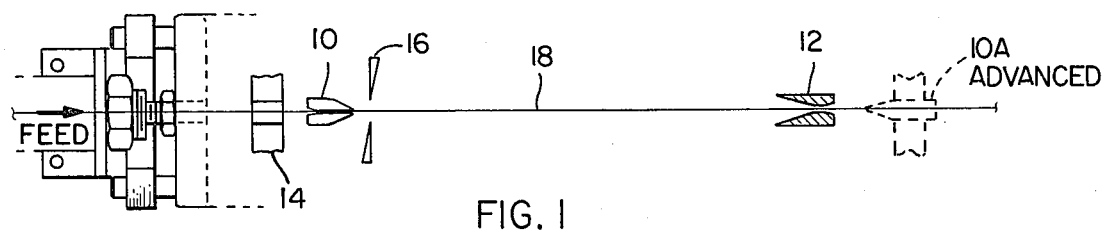
FIG. 1 is a schematic view of the string indexing mechanism of the present invention.

Shown in FIG. 1 is a means for string supply, tensioning and positioning which means may be generally viewed as a means for indexing a length of string into a proper condition and position for use in later operations. String is fed to said indexing means from the left of FIG. 1 (from that area denoted as FEED).

The string indexing procedure begins by the pulling of string 18 through holding element 14 and string advance element 10. This is done manually to prime the machine prior to automation.

When this is completed the machine is turned on and element 10 moves to the right pulling string 18 through element 14. It continues to the right until it goes through guide element 12. When element 10 is completely through element 12, said element 12 closes (under spring pressure) onto string 18.

After element 12 closes on string 18, element 10 is opened and returned to the left — going around the guide element 12 so that it holds the string stretched to it from the holding element 14.

String advance element 10 then proceeds to the left to original starting position until it is closed upon string 18, where it remains until the scissor cuts the thread and the stitching cycle is completed. At this time the string advance mechanism is cycled for another operation.

Figure 2:
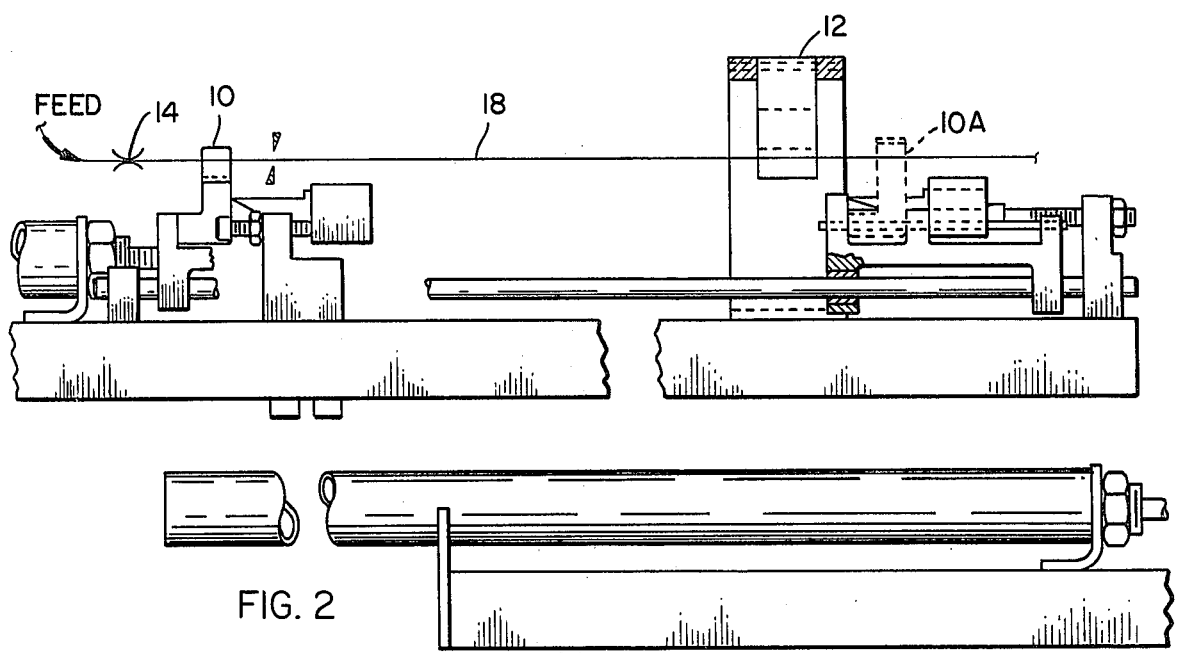
FIG. 2 is a longitudinal cross-sectional view of FIG. 1, including additional elements in the illustration thereof.
Figures 8A, 8B:
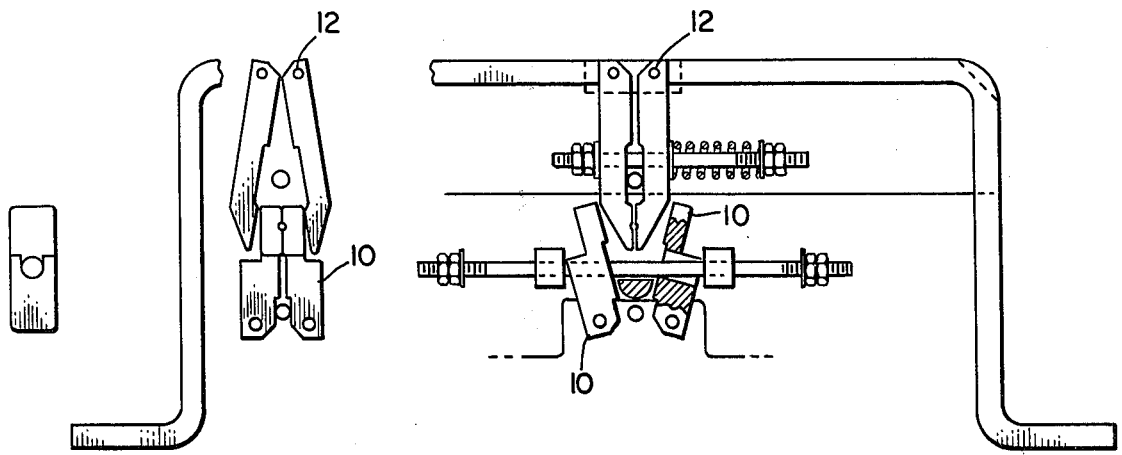
FIG. 8A illustrates the relationship between the string advance element and the guide element, as the advance element moves toward the string feed area.
FIG. 8B illustrates the relationship between the string advance element and the guide element as the guide element moves away from string feed area.

The schematic illustration in FIG. 1 is shown in fuller mechanical detail in FIG. 2. It is to be noted that elements 12 and 14 interact in order to tension the string 18 to a desired degree.

Figures 3, 5, 6:
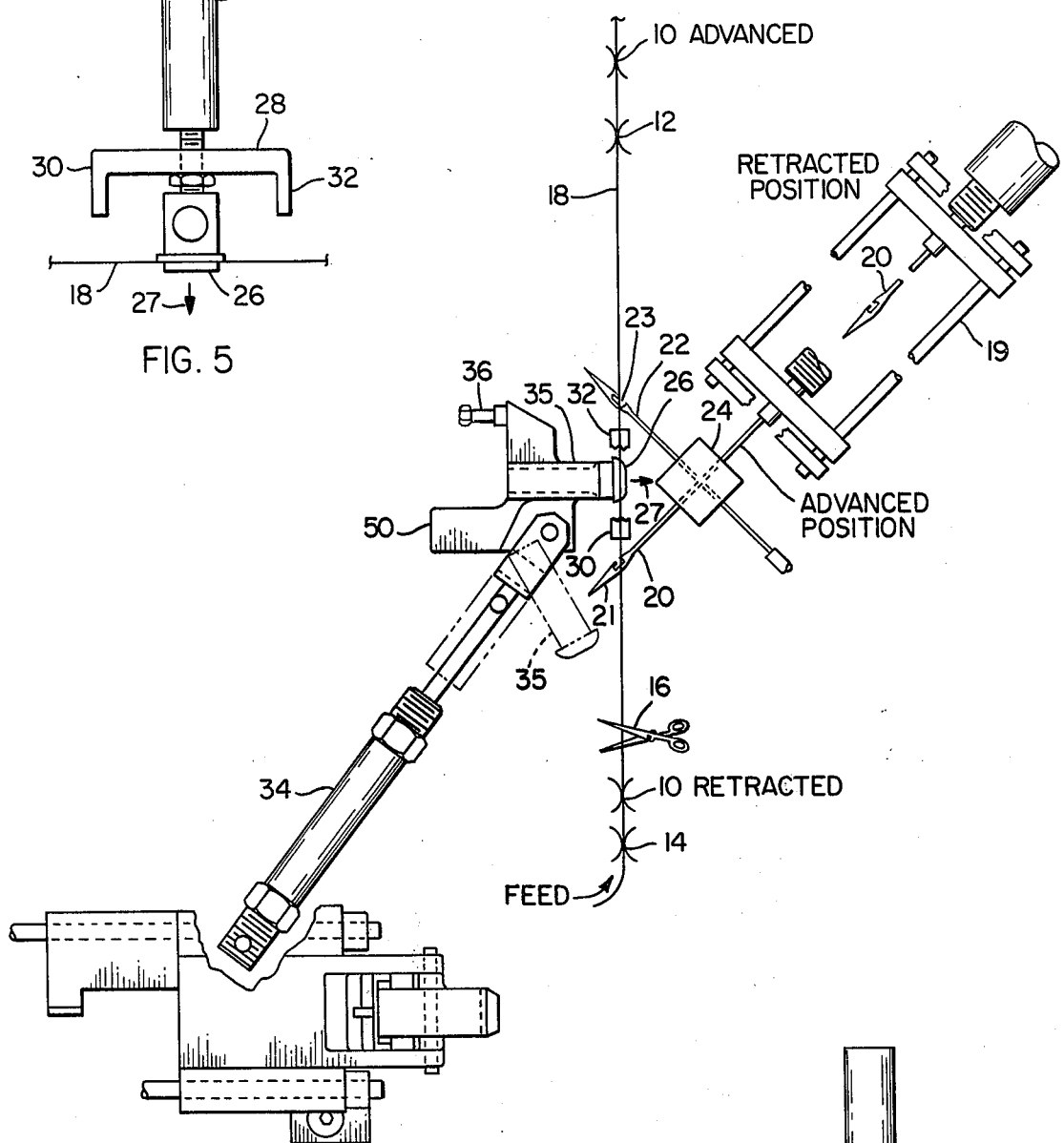
FIG. 3 illustrates, in partial schematic view, the basic stitching and string positioning mechanism of the present invention.
FIG. 5 is a cross-sectional view of the means for string displacement relative to the position of the eyelets of the two needles.
FIG. 6 is a side cross-sectional view of the illustration of FIG. 5.

Referring to FIG. 3, a segment of organic polymeric foam material suitable for tampon manufacture, hereinafter known as pre-form 24 is shown impaled upon perpendicularly displaced needles 20 and 22. Needles 20 and 22 possess at their respective distal ends, open, hook-shaped eyelets 21 and 23, which are illustrated in position to engage string 18 in a manner to be described hereinbelow.

At their proximal ends, needles 20 and 22 are provided with reciprocating means for advancing and retracting through pre-form 24. Such reciprocating means may comprise a wide variety of sources of motive power including electric motors, combustion engines, hydraulic and pneumatic cylinders and the like, and the invention should not be construed as limited to a particular source. For purposes of illustration, the motive source is depicted herein only with respect to needle 20, which is shown with reciprocating means 19, representing a vacuum cylinder.

Both needles 20 and 22 are provided with identical synchronized reciprocating means which serve to guide as well as actuate their simultaneous movement. Further, to facilitate their simultaneous operation, needles 20 and 22 enter pre-form 24 at right angles at each other, however, their paths are displaced a slight distance apart, such as, for exmple 3/16 of an inch.

Referring further to FIG. 3, it is noted that eyelets 21 and 23 of the needles 20 and 22, at their point of greatest advance, move slightly past the string 18. At this point, a string holding element 26, through which string 18 passes, serves to preliminarily position string 18 with respect to eyelets 21 and 23. More particularly, and referring as well to FIG. 5, it is noted that element 26 is capable of a selective movement in the direction illustrated by the arrow 27 in FIGS. 3 and 5. By virtue of this movement, which is on the order of about ¼ of an inch, string displacement elements 30 and 32 are caused to engage the string 18, slightly displacing it to the right (with reference to the vertical positioning of FIG. 3) and thereby effectuating the simultaneous engagement of the string 18 within said eyelets 21 and 23, as said eyelets begin their return motion toward pre-form 24.

In addition to the above function, holding element 26 firmly grasps and holds string 18 upon engagement therewith, and maintains its hold through the stitching process, finally releasing string 18 upon the formation of the knot. This hold facilitates the formation of the loop of string upon the retraction of needles 20 and 22 through pre-form 24. Further, the positioning of element 26 with respect to support element 35, which provides a passage for the application of suction to ends of string 18, enables the ends to pass through the loop to form the knot. The operation and sequencing of all elements discussed above is presented in detail hereinbelow.

It is to be noted that the apparatus at the lower left side of FIG. 3 serves primarily to position elements 26, 30 and 32 with respect to the stitching operation occurring at the right of FIG. 3. More particularly, it is to be noted that a support element 35 for said elements 26, 30 and 32 is adapted to swivel downwardly out of the path of the string 18 during that time of operation of the present device when the string advance element 10 is moving downward toward the holding element 14 in order to pull a new length of string into position for the next stitching cycle. Element 34 represents a vertical calibration means for the assembly associated with support element 35, while element 36 represents a horizontal calibration means for the assembly.

Once both eyelets have engaged the string, the needles are retracted, passing through the pre-form 24, and thereby pulling the string 18 through said pre-form. At the moment that retraction begins, the string 18 is cut by cutting means 16, thereby enabling the string to be pulled freely through pre-form 24. A total retraction of about 10 inches occurs. The resulting string configuration relative to pre-form 24 is shown in FIGS. 7A and 7B. It is noted that two loose ends, hereinafter termed pigtails 45 and 47, are formed.

As the operation of FIG. 3 occurs, the pre-form 24 is held in place by an essentially cubical retaining element 38. See FIG. 4. This retaining element 38 is provided with an entrance opening 39 and an exit opening 40. The purpose of the entrance opening is to permit the entrance of the first needle 20 into the pre-form, while the exit opening 40 serves to allow said needle 20 to pass through the opposite side thereof. The retaining element 38 is also provided with a second set of entrance and exit openings which permit the passage of the second needle 22 through the pre-form 24.

Figure 4:
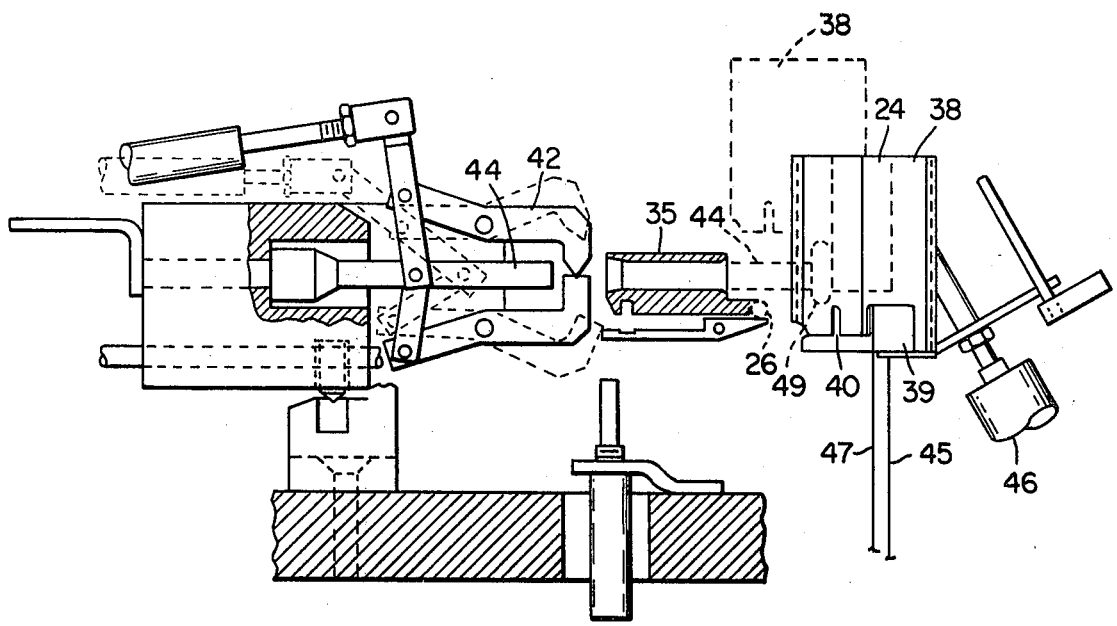
FIG. 4 is a cross-sectional view of the string looping and tightening mechanism of the present invention.

In FIG. 4, pigtails 45 and 47 are illustrated as hanging down below pre-form 24. Form this position, the retaining element 38 is lifted slightly upward (see dotted line position of element 38) in order to enable a vacuum tube 44 to advance through a channel provided in support element 35 to the right of FIG. 4, and to suck the pigtails 45 and 47 through predetermined loop 49 in the manner and configuration shown in FIGS. 7C and 7D. In FIG. 4, the predetermined loop 49 is schematically shown within element 38.

Figure 9:
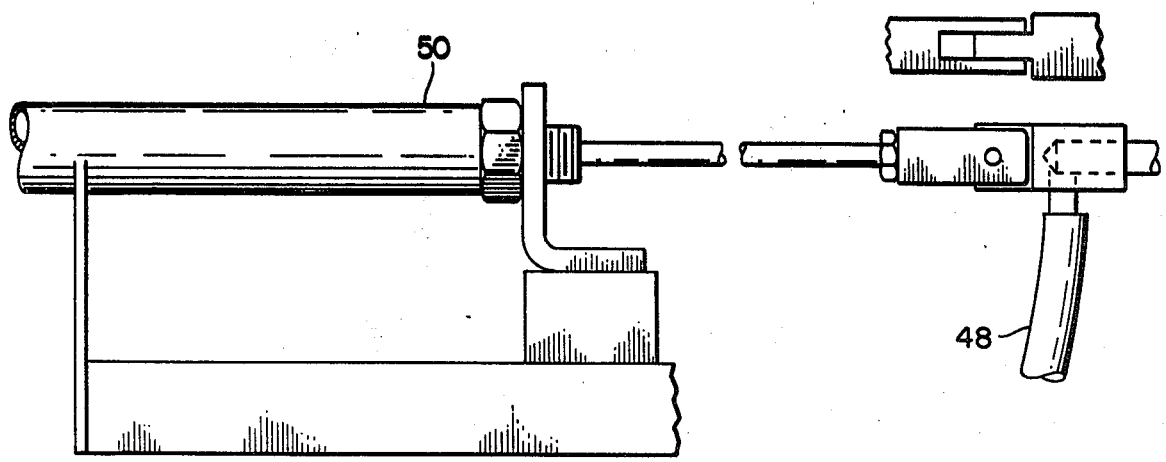
FIG. 9 is a schematic view of the pneumatic actuation means of the apparatus of FIG. 4.

After pigtails 45 and 47 are sucked through loop 49 and into tube 44, said pigtails are engaged and held by jaws 42. Jaws 42 are then retracted to the left by vacuum cylinder 50 (see FIG. 9) so as to tighten the pigtails within loop 49 (see FIG. 7D) to provide a firm "lark's head" knot engagement of the string 18 within and about pre-form 24. Upon the retraction of jaws 42 to place a predetermined tension on pigtails 45 and 47, holding element 26 releases loop 49 and the tightened knot is formed. Jaws 42 then continue their movement thereby drawing pre-form 24 completely through element 35 to remove the completely stitched pre-form from the stitching apparatus of the present invention and enable its deposit in a collection means, not shown. Likewise, the act of drawing pre-form 24 through element 35 by tension placed on pigtails 45 and 47 serves to test the strength and security of the "lark's head" knot within said pre-form.

Shown in FIG. 10 is one embodiment of the cutting means, schematically illustrated as scissors 16 in FIG. 3. The particular cutting means shown in FIG. 10 utilizes two blades 16A and 16B in order to cut the string 18 simultaneously with the retraction stroke of needles 20 and 22.

As noted earlier, a particular application of the present invention relates to the stitching of foams and other soft materials, such as may be utilized in a variety of applications, including the fabrication of tampons.

Accordingly, it is seen that the objects above enumerated in the Summary of the Invention have been efficiently attained by the above described embodiments.

While there have been herein shown and described the preferred embodiments to the present invention, it will be understood that the present invention may be embodied otherwise than is herein specifically illustrated or described and that within said embodiments certain changes in the detail and construction, and the form and arrangement of the parts may be made without departing from the underlying idea or principles of this invention within the scope of the appended Claims.

Having thus described our invention what we claim as new, useful and non-obvious and, accordingly, secure by Letters Patent of the United States is:

1. A stitching apparatus for attaching a finite length of string to a material such as a foam pre-form for use in a sanitary device comprising:
   a. a first needle having an open eyelet near the point thereof;
   b. means for advancing and retracting said first needle through said volume of material;
   c. a second needle having an open eyelet near the point thereof;
   d. means for advancing and retracting said second needle through said pre-form;
   e. means for selectively indexing said string into a line which permits the simultaneous engagement of said string by both of said eyelets of said needles; and
   f. means for cutting said string at the instant at which the retraction of said needles begins,
whereby, upon the full retraction of said needles, said pre-form is interiorly stitched along two lines, said lines, at one end of each, being exteriorly integral in the form of a loop and, at the other end of each comprising two ends hanging freely and protruding from said pre-form.

2. The apparatus as recited in claim 1 in which both of said advancing and retracting means comprise pneumatically actuated cylinders.

3. The apparatus as recited in claim 1 in which said indexing means includes means for transversely displacing said string, in the vicinity of said eyelets of said needles, in order to enhance the ease of engagement of said string by said eyelets.

4. The apparatus as recited in claim 1 in which said apparatus further comprises means for holding said pre-form at a proper position with respect to the points of said needles.

5. The apparatus as recited in claim 4 in which said apparatus further comprises suction means, adapted for actuation after said stitching has occurred, for pulling said ends of said string through said loop in order to form a knot.

6. The apparatus as recited in claim 5 in which said apparatus further comprises means for positioning said loop with respect to said ends prior to the application of said suction means.

7. The apparatus as recited in claim 6 in which said apparatus further comprises clamping means for engaging the ends of said string and for pulling them away from said positioning means in order to tighten said loop through and form said knot.

8. A method for stitching a finite length of string to a foam pre-form comprising the steps of:
   a. drawing the loose ends of said string through said pre-form in intersecting divergent perpendicular directions to form a loop on the side of their entry into said pre-form, whereby said ends protrude from said pre-form;
   b. passing said loose ends through said loop; and
   c. tightening said loop around said ends to form a knot.

9. The method as recited in claim 8 in which said ends are drawn through said pre-form by engagement and retraction with a pair of perpendicular directed reciprocable needles.

10. The method as recited in claim 9 in which said method further comprises the step of holding said pre-form at a proper position with respect to the points of said needles.

11. The method as recited in claim 8 in which said ends are passed through said loop by the application of suction thereto, and tightened by the application of tension by a mechanical grasping means communicating subsequently therewith.

12. The method as recited in claim 11 in which said method further comprises the step of positioning said loop with respect to said ends prior to the application of said suction.

13. The method as recited in claim 12 in which said tightening and tensioning step includes the applying of that degree of tension required in order to test the structural integrity of the stitched string within the pre-form.

14. The method as recited in claim 8 in which said method further comprises the step of indexing a continual length of string into adjacent alignment with said pre-form prior to said drawing step.

15. The method as recited in claim 14 wherein after said indexing step and upon the commencement of said drawing step, said continual length is severed to form said finite length and said loose ends.

* * * * *